(12) United States Patent
Hayashi et al.

(10) Patent No.: US 6,607,539 B1
(45) Date of Patent: Aug. 19, 2003

(54) ELECTRIC ENDOVASCULAR IMPLANT DEPOLYMENT SYSTEM

(75) Inventors: Reid K. Hayashi, Palo Alto, CA (US); Albert K. Chin, Palo Alto, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 12 days.

(21) Appl. No.: 09/860,717

(22) Filed: May 18, 2001

(51) Int. Cl.[7] ................................................. A61F 2/06
(52) U.S. Cl. ...................................... 606/108; 623/1.12
(58) Field of Search .................... 606/108; 623/1.11, 623/1.12, 1.13, 1.23

(56) References Cited

U.S. PATENT DOCUMENTS

| | | |
|---|---|---|
| 3,657,744 A | 4/1972 | Ersek |
| 3,868,956 A | 3/1975 | Alfidi et al. |
| 4,061,134 A | 12/1977 | Samuels et al. |
| 4,108,161 A | 8/1978 | Samuels et al. |
| 4,140,126 A | 2/1979 | Choudhury |
| 4,441,215 A | 4/1984 | Kaster |
| 4,512,338 A | 4/1985 | Balko et al. |
| 4,562,596 A | 1/1986 | Kornberg |
| 4,577,631 A | 3/1986 | Kreamer |
| 4,580,568 A | 4/1986 | Gianturco |
| 4,617,932 A | 10/1986 | Kornberg |
| 4,655,771 A | 4/1987 | Wallsten |
| 4,681,110 A | 7/1987 | Wiktor |
| 4,733,665 A | 3/1988 | Palmaz |
| 4,739,762 A | 4/1988 | Palmaz |
| 4,740,207 A | 4/1988 | Kreamer |
| 4,776,337 A | 10/1988 | Palmaz |
| 4,787,899 A | 11/1988 | Lazarus |
| 4,830,003 A | 5/1989 | Wolff et al. |
| 4,872,874 A | 10/1989 | Taheri |
| 5,078,726 A | 1/1992 | Kreamer |
| 5,078,735 A | 1/1992 | Mobin-Uddin |
| 5,104,399 A | 4/1992 | Lazarus |
| 5,108,407 A | 4/1992 | Geremia et al. |

(List continued on next page.)

FOREIGN PATENT DOCUMENTS

| | | |
|---|---|---|
| EP | 0 423 916 A1 | 4/1991 |
| EP | 0 461 791 A1 | 12/1991 |
| EP | 4 472 731 A1 | 3/1992 |
| EP | 0 667 132 A2 | 8/1995 |
| JP | 116792 A * | 4/2000 |

(List continued on next page.)

OTHER PUBLICATIONS

MedPRO Month (Sample Issue 1993); Transcatheter Cardiovascular Therapy.

Mirich, David, M.D.; Radiology, vol. 170 No. 3 Part 2 (1989); pp. 1033–1037; Percutaneously Placed Endovascular Grafts for Aortic Aneurysms: Feasibility Study[1].

Cragg, Andrew H., M.D.; Interventional Radiology, vol. 150 No. 1 (1983); pp. 45–49; Percutaneous Arterial Grafting[1].

Dotter, Charles T., M.D.; Technical Developments and Instrumentation; pp. 259–260; Transluminal Expandable Nitinol Coil Stent Grafting: Preliminary Report[1].

(List continued on next page.)

*Primary Examiner*—Ralph A. Lewis
(74) *Attorney, Agent, or Firm*—Fulwider Patton Lee & Utecht, LLP (57) ABSTRACT

A system for releasing a graft within vasculature that incorporates graft bindings severed by current-generated heat in a resistive wire element. In one aspect, the graft is held by bindings threaded through a resistive wire loop formed between conducting wires attached to opposite ends of a high resistive wire element. When an external current source is applied to the conducting wires, heat generated in the resistive wire element causes the bindings to sever, thereby allowing the graft to be released within vasculature.

19 Claims, 7 Drawing Sheets

U.S. PATENT DOCUMENTS

| | | |
|---|---|---|
| 5,151,105 A | 9/1992 | Kwan-Gett |
| 5,201,757 A | 4/1993 | Heyn et al. |
| 5,207,695 A | 5/1993 | Trout, III |
| 5,211,658 A | 5/1993 | Clouse |
| 5,219,355 A | 6/1993 | Parodi et al. |
| 5,236,446 A | 8/1993 | Dumon |
| 5,275,622 A | 1/1994 | Lazarus et al. |
| 5,282,824 A | 2/1994 | Gianturco |
| 5,306,294 A | 4/1994 | Winston et al. |
| 5,316,023 A | 5/1994 | Palmaz et al. |
| 5,360,443 A | 11/1994 | Barone et al. |
| 5,383,926 A | 1/1995 | Lock et al. |
| 5,387,235 A | 2/1995 | Chuter |
| 5,405,378 A | 4/1995 | Strecker |
| 5,425,765 A | 6/1995 | Tiefenbrun et al. |
| 5,453,090 A | 9/1995 | Martinez et al. |
| 5,456,713 A | 10/1995 | Chuter |
| 5,460,170 A | 10/1995 | Hammerslag |
| 5,464,419 A | 11/1995 | Glastra |
| 5,464,449 A | 11/1995 | Ryan et al. |
| 5,507,769 A | 4/1996 | Marin et al. |
| 5,522,836 A | 6/1996 | Palermo |
| 5,522,880 A | 6/1996 | Barone et al. |
| 5,527,355 A | 6/1996 | Ahn |
| 5,562,724 A | 10/1996 | Vorwerk et al. |
| 5,562,726 A | 10/1996 | Chuter |
| 5,571,170 A | 11/1996 | Palmaz et al. |
| 5,571,171 A | 11/1996 | Barone et al. |
| 5,571,172 A | 11/1996 | Chin |
| 5,571,173 A | 11/1996 | Parodi |
| 5,575,817 A | 11/1996 | Martin |
| 5,578,074 A | 11/1996 | Mirigian |
| 5,624,449 A | 4/1997 | Pham et al. |
| 5,656,036 A | 8/1997 | Palmaz |
| 5,676,685 A * | 10/1997 | Razavi ................. 606/194 |
| 5,713,948 A | 2/1998 | Uflacker |
| 5,755,773 A | 5/1998 | Evans et al. |
| 5,782,909 A | 7/1998 | Quiachon et al. |
| 5,873,907 A * | 2/1999 | Frantzen ................. 623/1 |
| 5,984,929 A * | 11/1999 | Bashiri et al. ........... 606/108 |
| 6,077,260 A * | 6/2000 | Wheelock et al. ........... 606/32 |
| 6,156,061 A * | 12/2000 | Wallace et al. ............ 623/1.11 |
| 6,165,178 A * | 12/2000 | Bashiri et al. ........... 606/108 |
| 6,206,888 B1 * | 3/2001 | Bicek et al. ............. 606/108 |
| 6,231,597 B1 * | 5/2001 | Deem et al. ............. 623/1.12 |
| 6,277,126 B1 * | 8/2001 | Barry et al. ............. 606/108 |
| 6,375,669 B1 * | 4/2002 | Rosenbluth et al. ........ 606/200 |

FOREIGN PATENT DOCUMENTS

| | | |
|---|---|---|
| WO | WO 91/12047 | 6/1991 |
| WO | WO 95/16406 | 6/1995 |
| WO | WO 95/34255 | 12/1995 |

OTHER PUBLICATIONS

Palmaz, Julio C., M.D.; Surgery (Feb. 1986); pp. 199–205; Expandable Intraluminal Vascular Graft: A Feasibility Study.

Lawrence, David D., M.D.; Cardiovascular Radiology (1987); pp. 357–360; Percutaneous Endovascular Graft: Experimental Evaluation[1].

Inoue, Kanji et al.; *Circulation* 1991, 84 (4 Suppl. II); II–421; Percutaneous Implantation of Aortic Endovascular Graft for Created Aneurysm: Animal Experiment.

Matsumae, Masaru, M.D.; Journal of Vascular Surgery (1988); pp. 38–44; An Experimental Study of a New Sutureless Intraluminal Graft wth an Elastic Ring That Can Attach Itself to the Vessel Wall.

Maass, D.; RSNA (1984); pp. 659–663; Radiological Follow–up of Transluminally Inserted Vascular Endoprostheses: An Experimental Study Using Expanding Spirals[1].

Dotter, Charles T., M.D.; Investigative Radiology (1969); pp. 329–332; Transluminally–Placed Coilspring Endarterial Tube Grafts.

Cragg, Andrew, M.D.; Radiology (1983); pp. 261–253; Nonsurgical Placement of Arterial Endoprostheses: A New Technique Using Nitinol Wire[1].

Bettmann, Michael A., M.D.; Scientific Sessions; pp. 161–202; Cardiovascular.

* cited by examiner

ELECTRIC ENDOVASCULAR IMPLANT DEPOLYMENT SYSTEM

BACKGROUND OF THE INVENTION

This invention relates to a system and method for implanting a prosthesis, and more particularly, to a method for releasing a graft within a corporeal lumen.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids. In some cases, the damaged lumen is repairable only with the use of a prosthesis such as an artificial vessel or graft.

For repair of vital vessels such as the aorta, conventional surgery may be significantly life-threatening. Techniques known in the art which tend to minimize dangers to the patient include a procedure in which a graft resembling the natural vessel is placed within the diseased or obstructed section of the natural vessel.

More specifically, it is known within the art to provide a prosthesis for intraluminal repair of a vessel. In intraluminal vessel repair, the prosthesis is advanced, in a radially compressed configuration, intraluminally through the vessel to the repair site using a delivery catheter. After being properly positioned at the repair site, the prosthesis is deployed in its expanded state within the vessel so that the prosthesis traverses the diseased portion to thereby repair the vessel. The prosthesis is secured within the vessel with hooks or staples that are either self-expanding upon deployment or are mechanically extended utilizing balloon dilation.

Various methods of deployment of the graft once it is positioned at the repair site are known in the art. One method utilizes a sheath that holds the graft in a radially compressed configuration until it is removed therefrom. Another method utilizes a mechanical release system composed of a retractable wire or control cords to release the graft from its compressed configuration. A third method utilizes an electrolytic release system which employs a power-induced difference of potential to cause erosion of metal binding straps that hold a graft in a radially compressed state.

A drawback of the sheath method is the potential, in certain circumstances, for cocking or longitudinal movement of the graft caused when the sheath is retracted. A drawback of the mechanical release systems is the potential for entanglement or a stress-induced failure when the release wire or cords are retracted or when the graft is advanced within the vessel. A drawback of the electrolytic release system is that it can potentially take from 30 seconds to 5 minutes for the bindings retaining a graft to erode after application of the external voltage device.

Accordingly, there is a need for a device and associated method that avoids the potential shortcomings of conventional sheath systems and the potential failures of conventional mechanical systems, while enabling the graft to be released accurately and expeditiously within vasculature. The present invention fulfills these and other needs.

SUMMARY OF THE INVENTION

Briefly, and in general terms, the present invention provides a new and improved device and method for releasing a graft within vasculature. In one aspect, the invention employs a resistive wire element which, when heated, severs bindings retaining a graft in a radially compressed configuration. The present system can be configured to release the graft bindings simultaneously or in any desired order. The present system operates to release a graft in an expedient manner and can be incorporated for use in existing prosthesis implant systems which utilize a sheath, mechanical release, or electrolytic erosion mechanism with only minor modifications to the delivery catheter and graft material.

In another aspect of the invention, conducting wires are used to deliver current to a resistive wire element which is placed in a looped configuration. The conducting wires extend from external a patient's body to a position adjacent the resistive wire. The resistive wire element can be made of material such as nichrome. The conducting wires can be made from standard circuitry wiring known in the art of medical electronics (i.e. copper with cladding). When heated by current supplied by an external voltage device, the resistive wire element severs the binding material which is threaded through the resistive wire loop. With the binding material cut, the graft is free to expand and secure itself to the vessel or be secured thereat by balloon dilation.

The graft can be tubular, bifurcated or modular. Preferably, the graft embodies woven polyester, or another material suitable for placement in the body such as PTFE, that allows the binding material to be threaded through the graft to engage the resistive wire loop.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

As shown in the exemplary drawings and for purposes of illustration, the invention is embodied in a device and method for releasing a graft from a radially compressed configuration into an expanded state within vasculature of a body. In one aspect, the implant deployment system includes a catheter and an expandable graft, and has associated therewith a method for releasing the graft within vasculature. It is contemplated that the present invention includes a catheter with conducting wire lumens that facilitate application of an external voltage device to resistive wire elements in direct contact with graft bindings to thereby release the graft from a contracted state.

Figure 1:
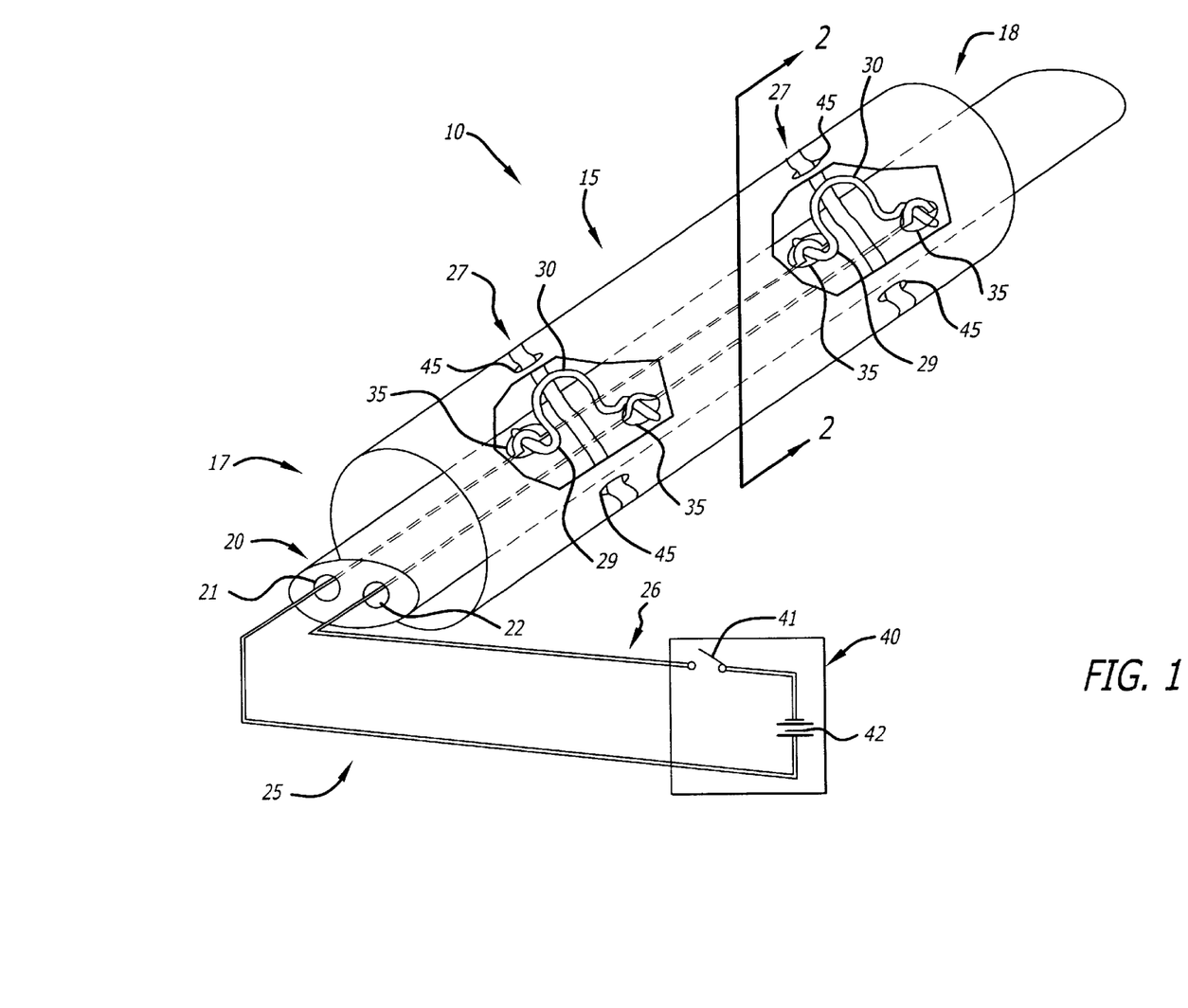
FIG. 1 is a perspective view, depicting a graft deployment system of the present invention with a portion of the graft material cut away to show the bindings threaded through the graft wall and resistive wire loops.

Referring to FIG. 1, there is shown a deployment system 10 for deploying a graft 15 within vasculature, the deployment system 10 including an inner shaft 20 having a pair of conducting wire lumens 21, 22, each of which are adapted to receive a conducting wire 25, 26. The system further includes resistive wire elements 29 and an external power source 40. The delivery system 10 may be used in conjunction with a conventional catheter (not shown) which may include structure for receiving and overlaying the graft 15 during advancement of the system 10 through vasculature.

In one aspect of the invention, the graft 15 is held in a radially compressed configuration about the inner shaft 20 by bindings 27. Each binding 27 is looped around the graft 15 and placed into engagement with a resistive wire element 29 by threading the binding 27 through the resistive wire loop 30 formed between the conducting wires 25, 26 and resistive wire element 29. Thereafter, the ends of the bindings 27 are pulled tight to collapse the graft 15 and are stitched to the graft 15 and knotted 28 (See FIG. 2A). One resistive wire element 29 is provided for each binding 27 used to secure the expandable graft 15 in its compressed state.

The resistive wire elements 29 are contemplated to be made of a highly resistive metal that is heated to an elevated temperature when current is passed therethrough. The external power source 40 includes an external voltage device 42 and a switch 41 allowing current to be delivered to the resistive wire elements 25, 26. The conducting wires 25, 26, resistive wire elements 29 and external power source 40 cooperate to facilitate the release of the graft 15 so it may be accurately implanted in a lumen.

Figure 2A:
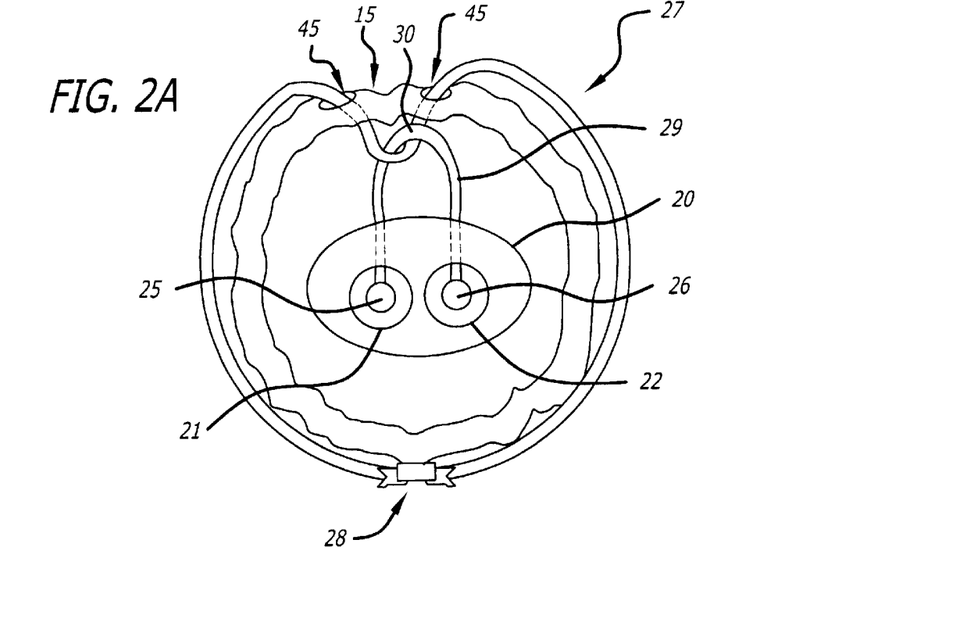
FIG. 2A is a cross-sectional view along line 2—2 of FIG. 1.
Figure 2B:
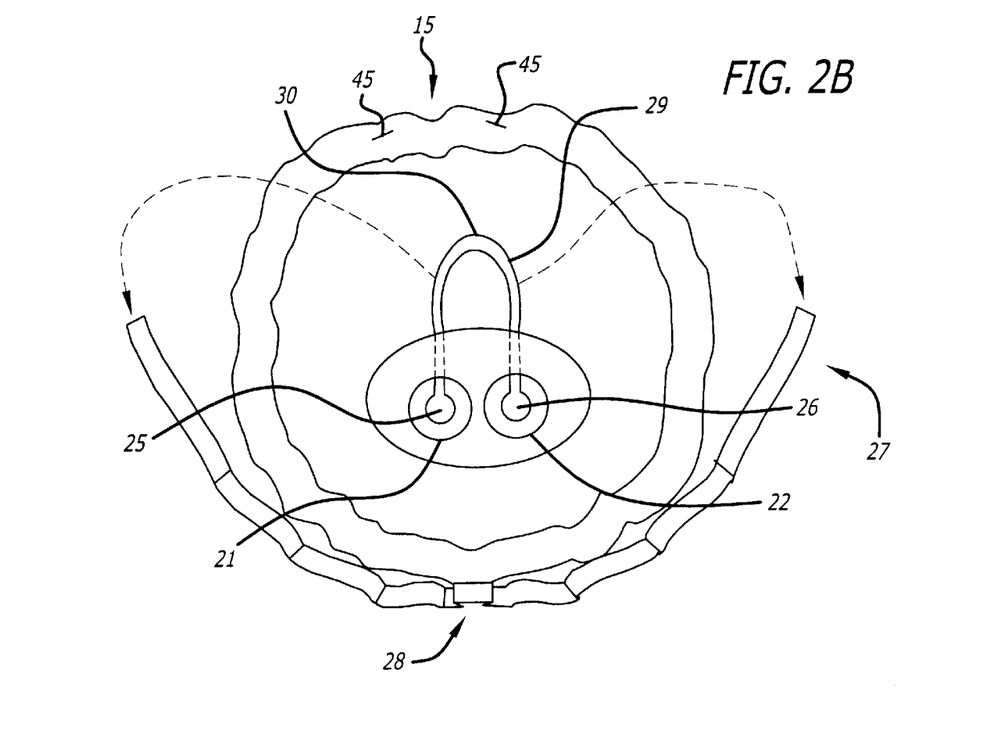
FIG. 2B is a cross-sectional view, depicting the system shown in FIG. 2A after an application of external voltage device.

Referring to FIGS. 2A and 2B, with the switch 41 of the external power source 40 open, the external voltage device 42 is not applied to the resistive wire elements 29 and the graft 15 remains in its contracted state. When the switch 41 of the external power source 40 is closed, the voltage is applied to the resistive wire elements causing them to heat. When the resistive wire elements 29 reach a critical temperature, they burn through the graft bindings 27, thereby releasing the graft 15. The graft 15 can then expand under its own forces, if self-expanding, or be expanded by balloon dilation.

Figure 3:
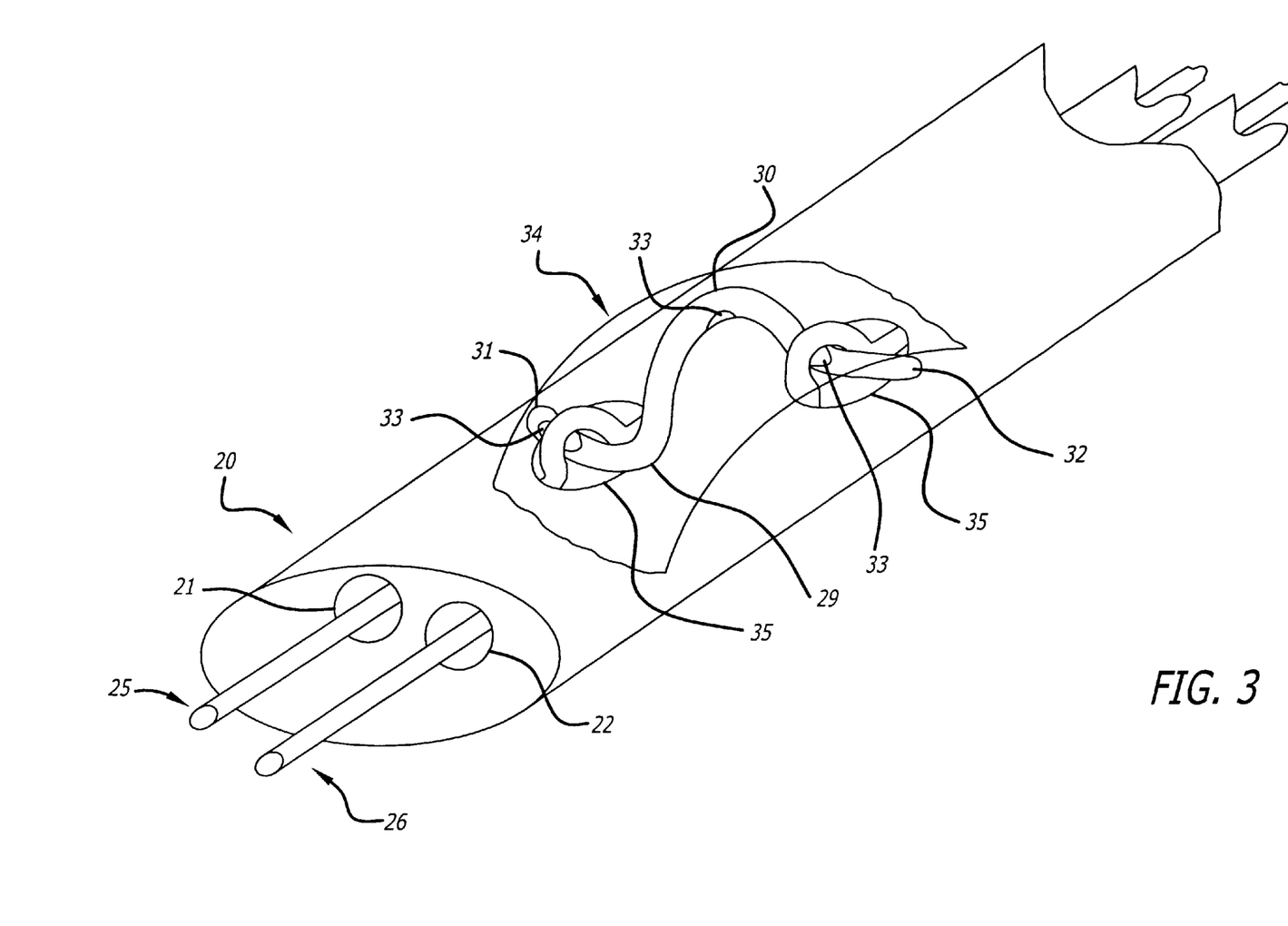
FIG. 3 is a perspective view, depicting the resistive wire loop formed by conducting wires and a resistive wire element.

Referring to FIG. 3, in one embodiment, each resistive wire element 29 is configured to have a portion of its alternate ends 31, 32 that lies transverse to a resistive wire exit opening 35 in the conducting wire lumen 21, 22. The conducting wires 25, 26 are configured so that they are disposed within the conducting wire lumens 21, 22 of the catheter inner shaft 20. Each conducting wire 25, 26 exits its respective conducting wire lumen 21, 22 through the resistive wire exit opening 35, where it makes contact with alternate ends 31, 32 of the resistive wire element 29. The conducting wires 25, 26 are attached to the resistive wire elements 29 by method of wire wrap, solder or other mechanical attachment to form the resistive wire loop 30 through which a graft binding 27 is threaded. Each conducting wire passes back through the same resistive wire exit opening 35 of the conducting wire lumen 21, 22 through which it exited. The conducting wires 25, 26 then pass through the conducting wire lumen 21, 22 of the catheter inner shaft 20 until they reach the next set of resistive wire exit openings 35, where they form another resistive wire loop 30 with the next resistive wire element 29. Finally, each conducting wire 25, 26 reenters the conducting wire lumen 21, 22 by again passing through the same resistive wire exit opening 35 and back into the conducting wire lumen 21, 22, where they advance distally within the catheter inner shaft 20. By so configuring the resistive wire elements 29, the graft 15 is locked to the catheter inner shaft 20 both radially and axially since the graft bindings 27 are threaded through the resistive wire loops 30 when the graft 15 is secured in its contracted state.

In a preferred embodiment, the conducting wires 25, 26 are typical copper wires with a diameter of approximately 0.008 inches (0.02 cm) and a length of approximately 19.7 inches (50.0 cm) so that they may be long enough to be connected to the external voltage device 40. The resistive wire elements 29 are made from nichrome or any other material having similar properties and have a diameter of approximately 0.008 inches (0.02 cm) and a length of approximately 0.39 inches (1.0 cm). The graft bindings 27 are be made of suture or any other material having similar properties. The graft 15 embodies an expandable tubular member having superior 17 and inferior 18 extremities. However, the graft 15 can also be bifurcated or modular in construction. The external power source 40 may include four 1.5 Volt AA batteries.

Additionally, in a preferred embodiment, the graft bindings 27 are configured to pass through the walls of the graft 15 via graft binding passageways 45. Since the graft 15 is contemplated to be woven, it includes warp and weft yarns which are separated to allow passage of the graft bindings 27 through its walls. Graft binding passageways 45 are provided by separating warp and weft yarns near, for example, the superior end 17 and the inferior end 18 of the graft 15. Each of the graft binding passageways 45 may include two sets of closely spaced warp and weft yarns which are individually separated to allow passage of the graft binding 27 through the walls of the graft 15, wherein one of two sets of warp and weft yarns serves as an exit and the other as an entrance. It is also contemplated that each graft binding passageway 45 may consist of a single set of warp and weft yarns that is separated to thereby provide both an exit and entrance for the graft binding 27 through the walls of the graft 15. In order to prevent damage to the graft 15 from the heat generated in the resistive wire loop 30, the resistive wire element 29 is coated with a material, such as flourinated ethylene propylene (FEP) or polytetraflouroethylene (PTFE). The coating is removed in selected areas 33, thereby allowing contact between the conducting wires 25, 26 and the resistive wire element 29 and between the resistive wire element 29 and the graft bindings 27.

In an alternate embodiment, the resistive wire element 29 is not coated and the graft 15 is protected from the heat generated in the resistive wire loop 30 by a heat shield 34 (shown in FIG. 3 as a translucent strip of material for illustrative purposes) made of a material such as high temperature aramid insulating paper such as sold under the tradename NOMEX from DuPont. The heat shield is joined to the catheter inner shaft to facilitate its removal once the graft is implanted.

Figure 4:
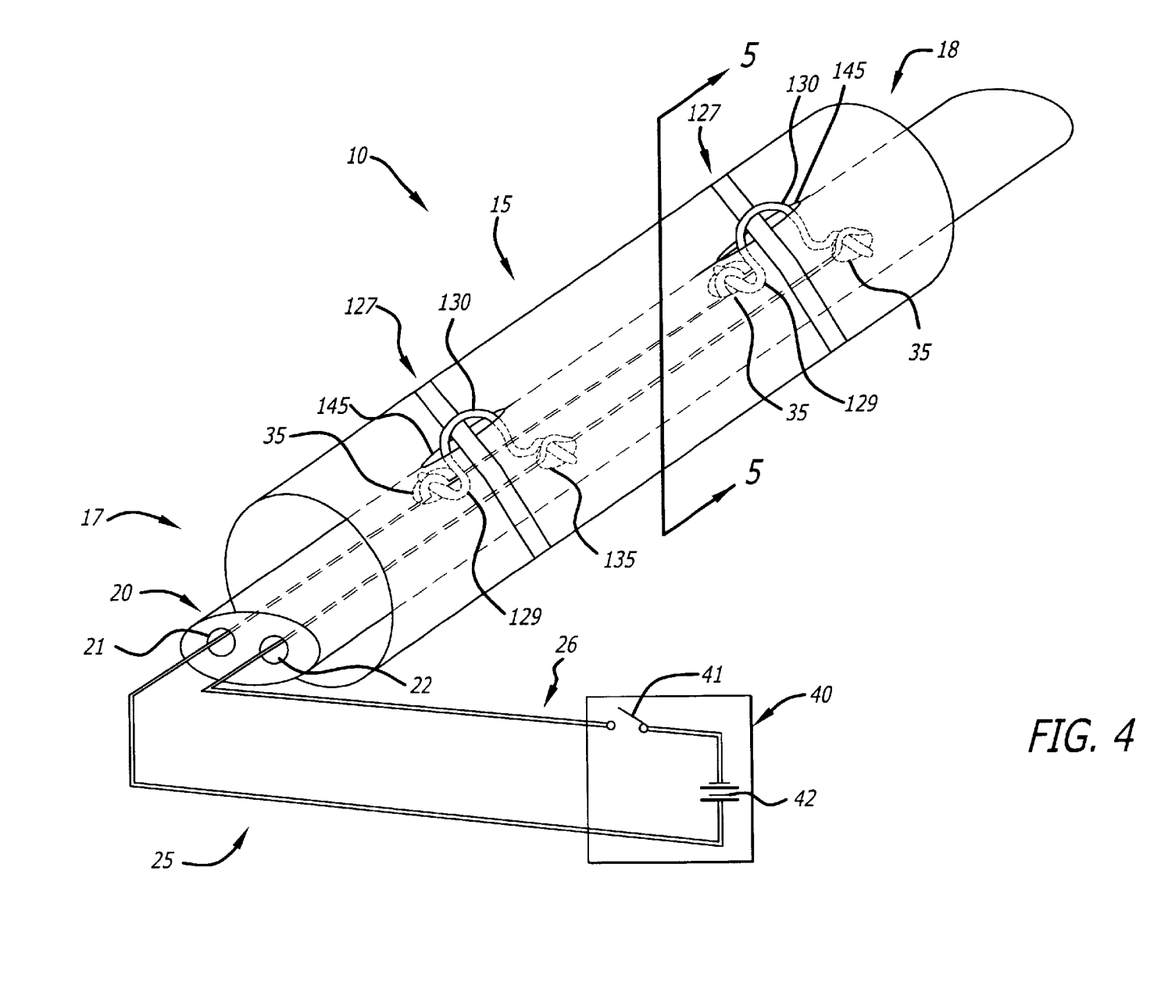
FIG. 4 is a perspective view depicting an alternate embodiment of the invention shown in FIG. 1 showing the bindings threaded through the resistive wire loops which pass through the graft wall.
Figure 5A:
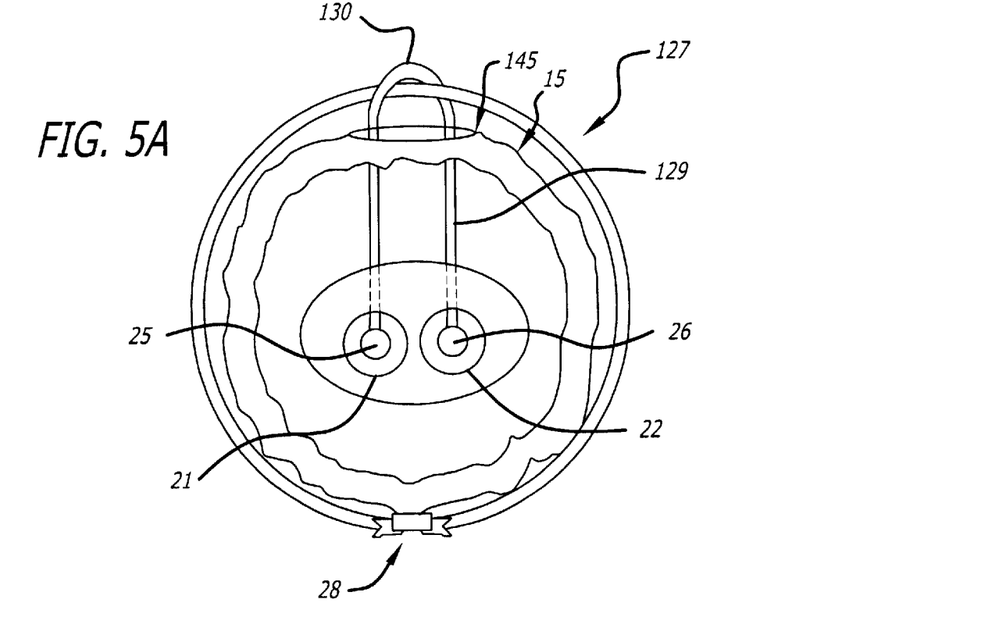
FIG. 5A is a cross-sectional view along line 5—5 of FIG. 4.
Figure 5B:
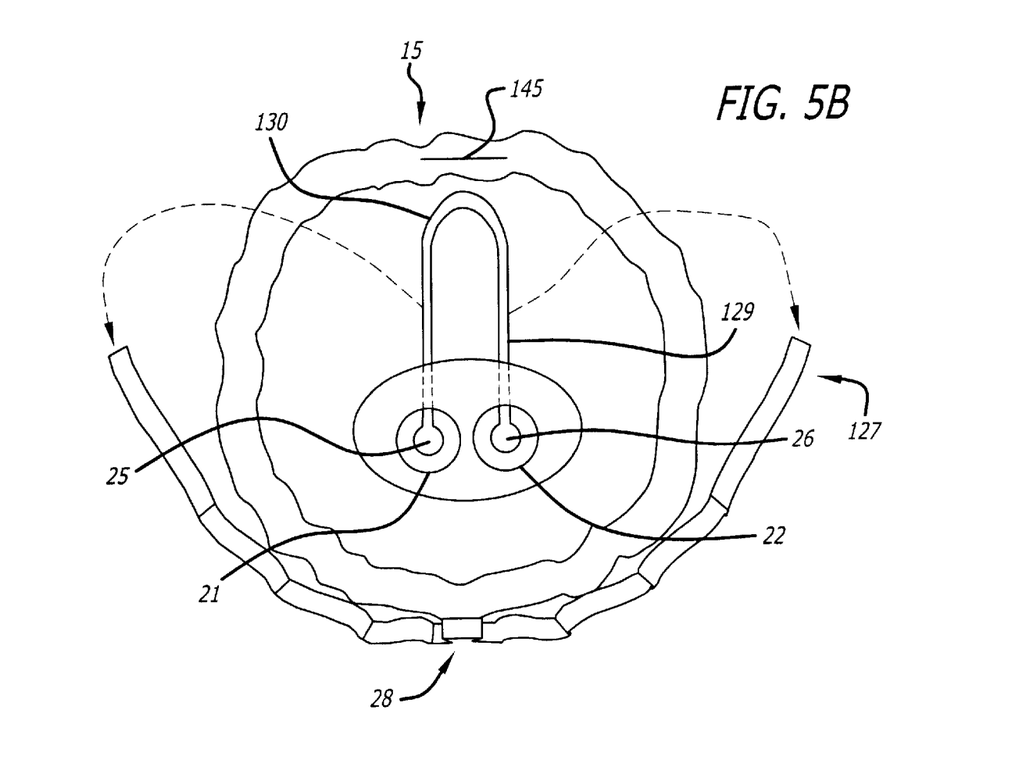
FIG. 5B is a cross-sectional view, depicting the system shown in FIG. 5A after an application of external voltage device.

In another alternate embodiment shown in FIGS. 4, 5A, and 5B, the graft bindings 127 do not pass through the walls of the graft 15. Instead, the resistive wire elements 129 pass through the walls of the graft 15 via resistive element passageways 145, thereby allowing the graft bindings 27 to be threaded through the resistive wire loops 130. Protection of the graft 15 from the heat generated in the resistive wire loop 130 can be provided by coating the resistive wire element 29 or a heat shield 34.

Figure 6:
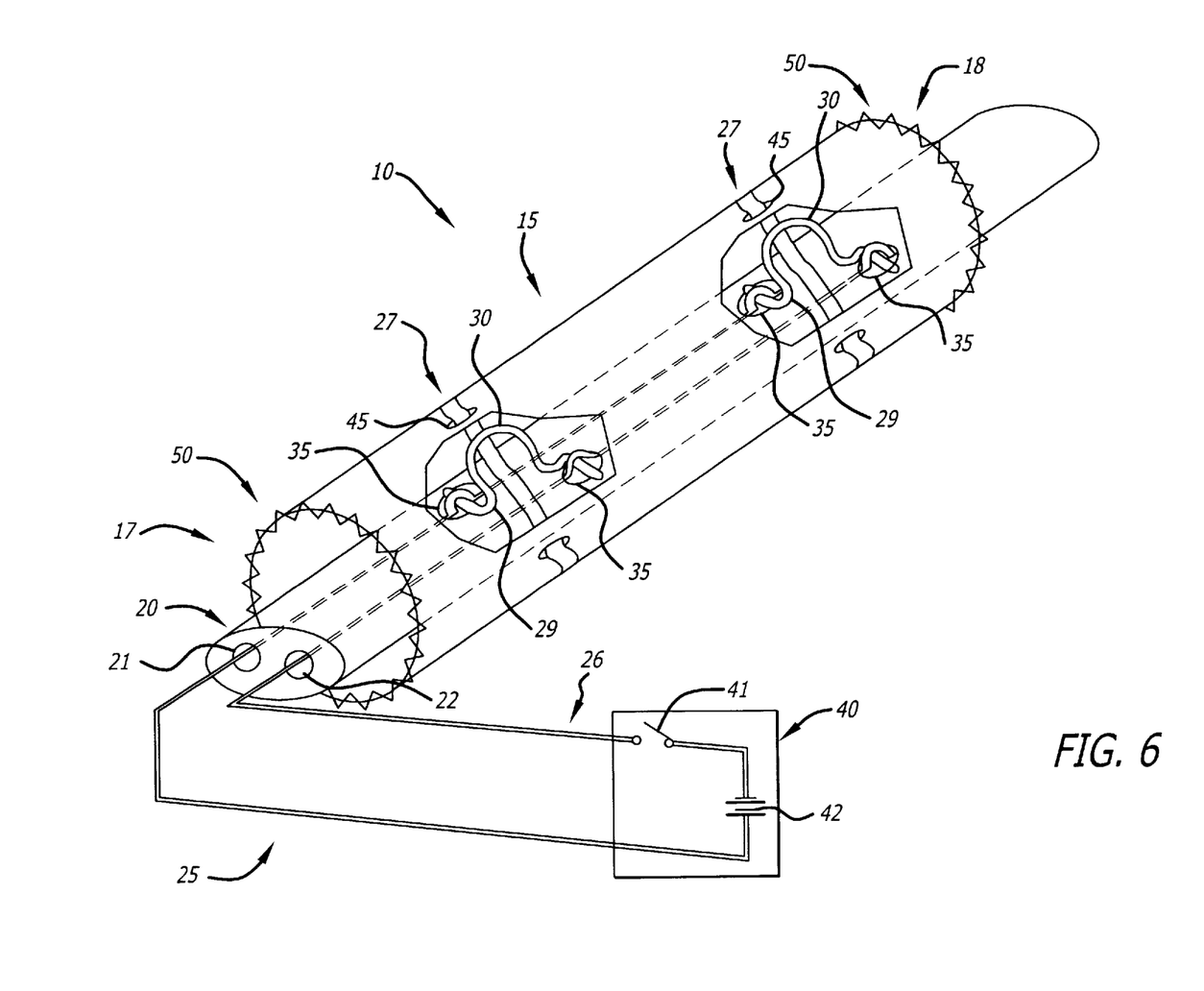
FIG. 6 is a perspective view depicting an alternate embodiment of the invention shown in FIG. 1 showing attachment systems at the superior and inferior ends of the graft.

In another alternate embodiment shown in FIG. 6, expandable attachment systems 50 are secured to the superior 17 and inferior 18 ends of the graft 15. The attachment systems 50 are provided with wall engaging members which may be covered by a sheath or capsule assemblies (not shown). It is to be recognized, however, that although the present invention has been described as being employed to receive a graft with attachment systems, any medical device can be adapted to be used in combination with the deployment system 10 of the present invention.

Figure 7:
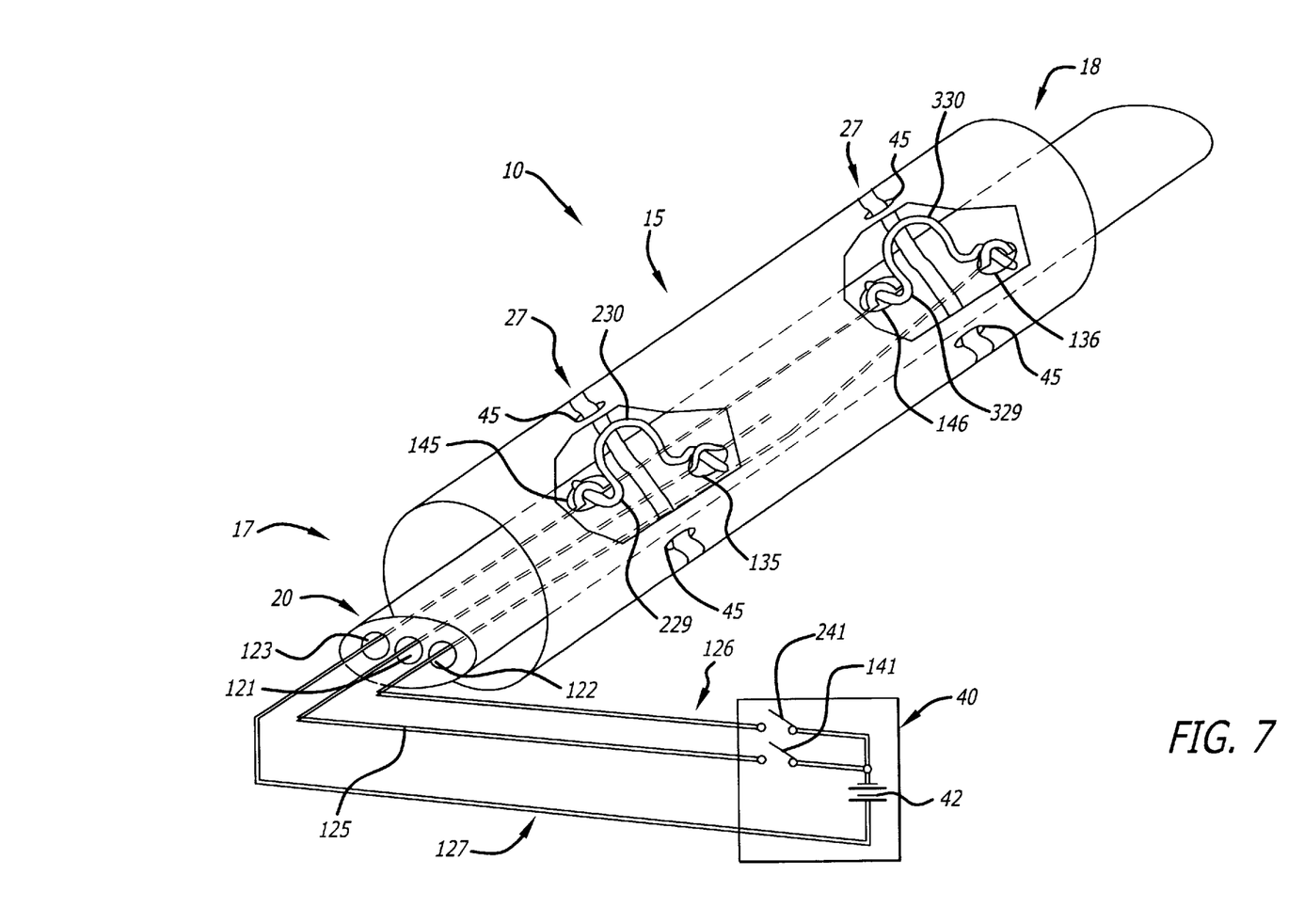
FIG. 7 is a perspective view depicting an alternative embodiment of the invention shown in FIG. 1 providing individual control of the graft bindings.

In another alternate embodiment, the delivery system 10 is contemplated to include three conducting wires, as shown in FIG. 7. A superior conducting wire 125 is configured to exit a superior conducting wire lumen 121 through a superior resistive wire exit opening 135 and make contact with a superior resistive wire element 229. A second conducting wire, an inferior conducting wire 126, is configured to exit an inferior conducting wire lumen 122 through an inferior resistive wire exit opening 136 and make contact with an inferior resistive wire element 329. A third conducting wire, the common conducting wire 127, exits a common conducting wire lumen 123 through both a superior resistive wire exit opening 145 and an inferior resistive wire exit opening 146 to provide a common return path for both resistive wire elements 229, 329. The resulting superior resistive wire loop 230 and inferior resistive wire loop 330, in conjunction with a first power switch 141 and second power switch 241, respectively, allow the external voltage device 42 to be applied separately to thereby provide individual control of the deployment of the superior end 17 and inferior end 18 of the graft 15.

In order to have greater flexibility, the three conducting wire system may be employed. That is, by applying the external voltage device 42 between the common conducting wire 127 and the superior conducting wire 125 prior to applying the external voltage device 42 between the common conducting wire 127 and the inferior conducting wire 126, the superior end 17 of the graft 15 can be released from its compressed state before so releasing the inferior end 18. Thus, attachment of the superior end 17 of the graft 15 within a lumen can be achieved prior to the attachment of the inferior end 18 within the lumen. The external voltage device 42 can then be applied between the common conducting wire 127 and the inferior conducting wire 126 to attach the inferior end 18 of the graft 15 within the lumen. The three conducting wire system can also be used to attach the inferior end 18 of the graft 15 within the lumen first.

As will be readily apparent to one of skill in the design of endovascular implant deployment systems, the various embodiments of the deployment system of the present invention may be used with a self-expanding attachment system as well as with a balloon dilation system. In addition, while the foregoing discussion of the embodiment of the deployment system illustratively employed two graft bindings, a greater or lesser number of graft bindings may be accommodated. Moreover, the invention may readily be implemented with forms of graft bindings other than those illustrated herein.

While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention.

Accordingly, it is not intended that the invention be limited, except as by the appended claims.

What is claimed is:

1. A system for releasing a graft within a lumen, said system comprising:
   a graft;
   a delivery catheter adapted to be placed within the lumen;
   an attachment device releasably attaching the graft to the delivery catheter; and
   a release source for releasing the attachment device, the release source including one or more resistive wire elements and conducting wires;
   wherein the release source is electrical and facilitates near contemporaneous release of the graft from the attachment device; and
   the delivery catheter further comprising an inner catheter configured within the graft, the inner catheter including a conducting wire lumen to receive the conducting wires and at least one opening in communication with each end of each resistive wire element, whereby each conducting wire exits the conducting wire lumen at a different opening to engage one of each resistive wire element, thereby forming one or more resistive wire loops.

2. The system of claim 1, wherein the graft has a first configuration and a second configuration, the first configuration compressed from the second configuration, and the attachment device further comprises one or more bindings retaining the graft in the first configuration.

3. The system of claim 2, wherein the conducting wires connect each resistive wire element to a switchable external voltage, whereby voltage-generated heat in each resistive wire element severs at least one of the bindings retaining the graft in the first configuration.

4. The system of claim 3, wherein a coating is selectively applied to the resistive wire element to thereby protect the graft from heat generated by the resistance wire element.

5. The system of claim 3, the attachment device further comprising one or more bindings, each secured at its midpoint to the graft, threaded through one of the resistive wire loops, and affixed at its ends to the graft.

6. The system of claim 5, wherein each of the bindings is threaded through one of the resistive wire loops such that the binding resides entirely exterior to the graft.

7. The system of claim 5, wherein each of the bindings passes through a wall of the graft to engage one of the resistive wire loops.

8. The system of claim 5, each resistive wire element further coated with a heat resistant material, wherein gaps in the material allow the conducting wires to make contact with each resistive wire element and each resistive wire loop to make contact with one or more graft bindings.

9. The system of claim 5, wherein a heat resistant shield is placed between each resistive wire loop and the graft.

10. The system of claim 1, comprising:
    the graft having a superior end and inferior end;
    the inner catheter having a conducting wire lumen having two sets of two openings each, one inferior set and one superior set;
    the attachment device including a superior binding and an inferior binding; and the release source including a superior resistive wire element and an inferior resistive wire element;

wherein each conducting wire exits a different inferior opening in the conducting wire lumen, engages the inferior resistive wire element and reenters the same inferior opening, thereby forming an inferior resistive wire loop and each conducting wire further exits a different superior opening in the conducting wire lumen, engages the superior resistive wire element and reenters the same superior opening, thereby forming a superior resistive wire loop.

11. The system of claim 10, the conducting wires providing a common path between the switchable external voltage and the superior resisitive wire loop and inferior resistive wire loop, whereby the switchable external voltage is applied to the superior resistive wire loop and inferior resistive wire loop simultaneously.

12. The system of claim 10, the conducting wires providing separate paths between the switchable external voltage and the superior resistive wire loop and inferior resistive wire loop, whereby the switchable external voltage can be applied to the superior resistive wire loop and inferior resistive wire loop in a non-simultaneous manner.

13. The system of claim 10, the conducting wire lumen having more than two sets of openings, the attachment device including more than two bindings, and the release source having more than two resistive wire elements, thereby forming more than two resistive wire loops.

14. The system of claim 1, wherein the graft further comprises one or more attachment systems secured to the graft, each attachment system having a first configuration and a second configuration, the first configuration compressed from the second configuration.

15. The system of claim 1, further comprising a shield placed between the graft and the attachment device.

16. A method for releasing a graft within a lumen using a delivery catheter being releasably attached to the graft by an attachment device in combination with an electrical release source, the release source including one or more resistive wire elements and conducting wires and the delivery catheter including an inner catheter with a conducting wire lumen to receive the conducting wires and at least one opening in communication with each end of each resistive wire element, comprising:

configuring each conducting wire to exit the conducting wire lumen at a different opening to engage one end of each resistive wire element thereby forming one or more resistive wire loops;

placing the graft and delivery catheter within vasculature of a patient; and activating the release source to automatically disengage the attachment device from the graft.

17. The method of claim 16, wherein the release source includes one or more resistive wire elements and conducting wires in communication with a voltage source and the activating step further comprises causing electricity to be passed from the voltage source to the resistive wire elements.

18. The method of claim 17, further comprising generating heat in the resistive wire element.

19. The method of claim 18, wherein the attachment device is placed in content with the at least one resistive wire element and further comprising allowing the heat generated by the resistive wire element to sever the attachment device.

* * * * *